(12) United States Patent
Wess et al.

(10) Patent No.: US 8,099,154 B1
(45) Date of Patent: Jan. 17, 2012

(54) APPARATUS FOR GENERATING FOCUSED ACOUSTICAL PRESSURE WAVES

(75) Inventors: Othmar Wess, Lengwill-Oberhofen (DE); Ernst H. Marlinghaus, Bottighofen (DE)

(73) Assignee: Storz Medical AG, Kreuzlingen (DE)

( * ) Notice: Subject to any disclaimer, the term of this patent is extended or adjusted under 35 U.S.C. 154(b) by 0 days.

(21) Appl. No.: 08/199,349

(22) Filed: Feb. 17, 1994

Related U.S. Application Data

(63) Continuation of application No. 08/058,796, filed on May 10, 1993, now abandoned, which is a continuation of application No. 07/499,406, filed on Jun. 14, 1990, now abandoned.

(30) Foreign Application Priority Data

Oct. 17, 1988 (DE) .................................. 38 35 318

(51) Int. Cl.
*A61B 17/225* (2006.01)
(52) U.S. Cl. ................. 600/427; 600/439; 601/2; 601/4
(58) Field of Classification Search .................. 600/427, 600/439; 601/2–4; 367/140–147, 151, 155, 367/157, 159, 163, 174, 175, 153; 128/24 EL, 128/660, 660.03; 73/625, 642
See application file for complete search history.

(56) References Cited

U.S. PATENT DOCUMENTS

| | | | |
|---|---|---|---|
| 3,587,038 A | 6/1971 | Massa | |
| 4,495,817 A * | 1/1985 | Hunt et al. | ...................... 73/624 |
| 4,526,168 A | 7/1985 | Hassler et al. | |
| 4,570,634 A | 2/1986 | Wess | |
| 4,697,588 A | 10/1987 | Reichenberger | |
| 4,807,627 A * | 2/1989 | Eisenmenger | ..................... 601/4 |
| 4,823,041 A | 4/1989 | Inoue et al. | |
| 4,844,079 A | 7/1989 | Naser et al. | |
| 4,928,672 A * | 5/1990 | Grasser et al. | ............ 128/24 EL |
| 4,947,830 A * | 8/1990 | Rattner et al. | ............ 128/24 EL |
| 5,160,336 A | 11/1992 | Favre | |

FOREIGN PATENT DOCUMENTS

| | | | |
|---|---|---|---|
| DE | 31 19 295 | | 12/1982 |
| EP | 0 108 190 | | 5/1984 |
| EP | 0 188 750 | | 7/1986 |
| EP | 0 251 797 | | 1/1988 |
| EP | 0 265 742 | | 5/1988 |
| JP | 1-254280 | | 10/1989 |
| SU | 1393489 | * | 5/1988 |
| SU | 1405885 | * | 6/1988 |

* cited by examiner

*Primary Examiner* — Ruth S Smith
(74) *Attorney, Agent, or Firm* — Barnes & Thornburg LLP

(57) ABSTRACT

An apparatus for generating focused acoustical pressure waves for therapeutical applications and, in particular, for destroying concrements, corporeal stone, etc., comprises a sound generating unit, which generates pressure waves in a coupling medium, a reflector which focuses the waves and having, if necessary, a locating unit for locating the concrements, corporeal stones, etc., to be destroyed. The sound generating unit is a corpus or body which is axially symmetrical to an axis running through the focal point and whose casing extends in the direction of the axis and is the emission area for the waves. The sound generating unit generates axially symmetrical pressure waves, the propagation direction of which is essentially perpendicular to the axis.

42 Claims, 5 Drawing Sheets

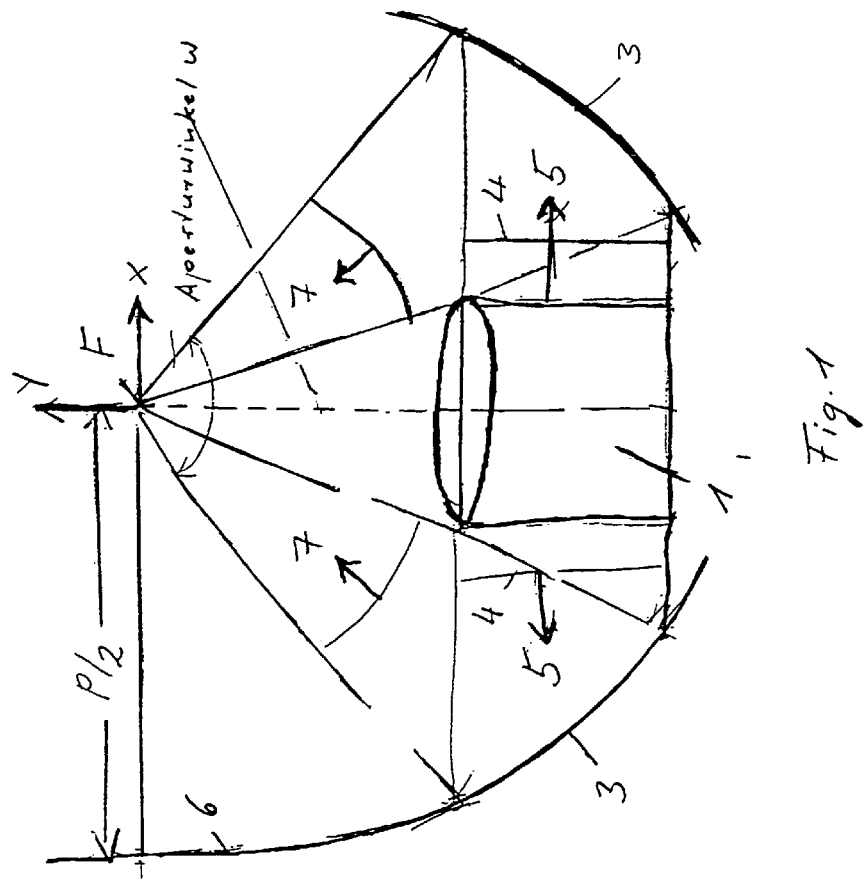
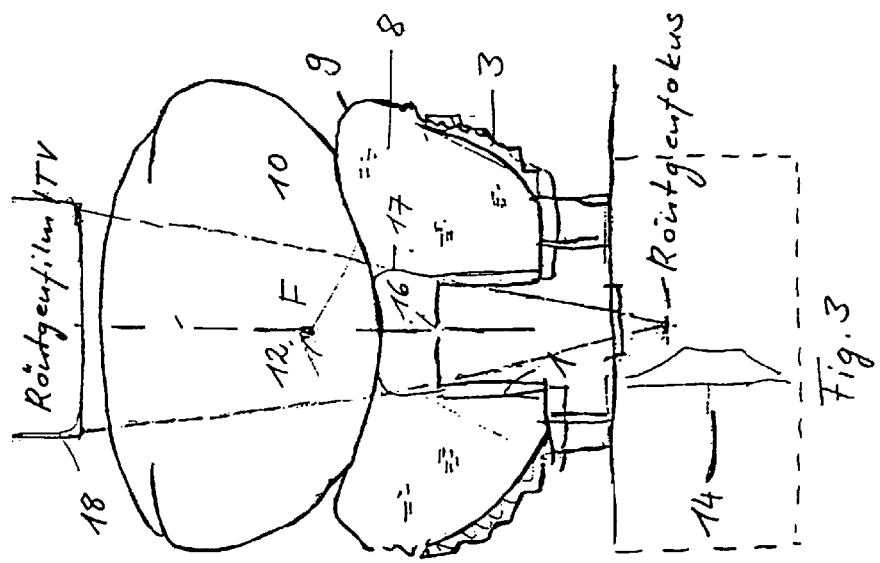

APPARATUS FOR GENERATING FOCUSED ACOUSTICAL PRESSURE WAVES

This is a Continuation of application Ser. No. 08/058,796, filed May 10, 1993 now abandoned which is a continuation of application Ser. No. 07/499,406, filed Jun. 14, 1990 and now abandoned.

The present invention relates to an apparatus for generating focused acoustical pressure waves for therapeutical applications and, in particular, for destroying concrements, corporeal stones, etc., by way of a sound generating unit which generates axially symmetrical pressure waves whose propagation direction is essentially perpendicular to an axis running through the focal point.

Apparatuses of this general kind are known, by way of illustration from the German A-documents 34 47 440; 31 19 295 (U.S. Pat. No. 4,526,168); 35 05 894; 35 02 751; 35 01 838; 34 43 383 and are employed again, by way of example, for extra-corporeal lithotripsy.

Extra corporeal lithotripsy and other therapeutical applications of sound wave fields, i.e. pulse sound waves or shock waves, are essentially based on the fact that high energy therapy waves with little energy density are coupled in the body and become therapeutically effective by focusing in a narrowly defined effective area, namely the focal zone of the focused wave field.

Thus, there are two problems that need to be solved in connection with apparatuses generating focusing sound wave fields for therapeutical applications:

1. Generating a high energy therapy wave with little energy density with the greatest possible efficiency, and
2. Focusing this therapy wave in as small as possible a volume range.

The degree of focusing of the therapy wave is determined by the temporal and spatial wave profile and the opening angle (aperture) of the wave field; the aperture for its part determines the energy density of the therapy field at point of entry into the body and the energy density in the focal zone. Both parameters for their part influence the pain effect and the success of the therapy as well as the confinement of the therapy effect to the desired area.

Essentially three different generating and focusing principles are used in knows devices for generating focused sound wave fields for therapeutical applications that serve, in particular, for extra-corporeal kidney stone and gallstone treatment:
  electromagnetic pressure wave generation,
  piezoelectric pressure wave generation,
  electrohydraulic shock wave generation.

These principles of generating wave fields have differing data with regard to effectiveness, life time, materials used, focal size, energy density, and the like.

None of the mentioned principles can meet all the demands satisfactorily. For this reason, none of the cited principles has been able to predominate.

By way of illustration, electromagnetic pressure wave generation has the drawback that plane waves are generated with it, which have to be focused through acoustic lenses or—in this connection reference is made to DE 34 47 440 A1 or DE 3501 838 A1—by means of a focusing reflector and, if need be, additional lenses following deflection by a reflector possessing no focusing effect.

Acoustic lenses of sufficient quality can, however, presently not be realized, at least not in practice, so that the resulting therapy field distribution is inferior to other processes with regard to the degree of focusing, the aperture angle and the size of the focal zone, but these processes, on the other hand, are unsatisfactory in other essential points, such as, by way of illustration, the longevity of the sound generator.

Moreover, in the known apparatuses for generating focused sound wave fields it is difficult to position a locating unit, by way of illustration, for kidney stones in the range of the apparatus without the locating unit disturbing the therapeutical wave field.

Although reflectors for wave fields have been known for a long time, with apparatuses for generating focused acoustical wave fields for therapeutical applications, they have hitherto only been used for focusing shock waves, which are generated by a spark gap, or for focusing plane wave fields, which are reflected by a non-focusing reflector. In this connection, reference is made, by way of illustration, to DE-PS 32 41 026 and DE 34 47 440 A1.

An object of the present invention is to provide an apparatus for generating focused acoustical wave fields for therapeutical applications and, in particular, for destroying concrements, corporeal stones, etc., in which the focused therapeutical wave field has a large aperture and an optimized focusing zone without having to accept limitations regarding the longevity of the sound generating unit or making the arrangement of a locating unit for corporeal stones, and the like, difficult.

The present invention is based on a fundamental concept of combining a shaped surface sound generating unit emitting an unfocused wave field, the energy density of which decreases with increasing distance from the sound generating unit, with a reflector for the wave field, which focuses the wave field.

An aspect of the present invention involves the employment of a sound generating unit which is a body that is axially symmetrical to an axis running through the focal point. The casing surface of this body extending in the direction of this axis is the emission area for the sound waves. By virtue of this arrangement, the energy density in the region of the sound generating unit is small so that the longevity of the apparatus of the present invention is not too greatly limited by wear of the sound generating unit.

The use of an acoustic reflector, compared with the use of acoustic lenses, has the advantage that highly effective acoustic reflectors are available, and focus the sound wave field with few aberrations.

In particular, the apparatus of the present invention has an emission area symmetrical to an axis running through the focal point and has the advantage that the sound wave field to be focused has a large aperture. In addition, a focused wave field is generated only outside a region that, by way of example, surrounds the axis running through the focal point conically. Therefore, the corporeal stone, etc., locating unit, which, may be an X-ray unit or an ultrasonic locating unit, can be without difficulty in the therapy-sound-wave-field region, i.e. within the emission area of the sound generating unit symmetrically surrounding the axis running through the focal point, and, in particular, without disturbing the sound wave field.

In this connection, it is especially advantageous that the present invention permits the use of a hollow body without difficulty so that the locating unit can be arranged not only in or on the sound generating unit, but also can be moved along the axis of the apparatus and/or rotated about this axis. In this manner, the locating unit can detect corporeal stones without difficulty and without errors caused by diffraction.

Another advantage of the present invention resided in the fact that the emission area of the sound generating unit generates a wave field with a temporal distribution, which can be focused in a true-phased manner, i.e. with a high degree of effectiveness in a small volume range.

Moreover, the shape of the reflector and, in particular, misalignments, etc., of the individual parts to one another, contrary to the reflectors known from DE OS 23 51 247 or the DE-PS 32 41 026, are not critical as they do not have to "image" an approximately dot-shaped wave-field in an also approximately dot-shaped wave field, but only have to focus an "extended" wave field and, in particular, a wave field of cylindrical symmetry.

A reflector form for the present invention can have the shape of a paraboloid of revolution, which cuts through the sound generating unit in the region of the axis running through the focal point.

However, it should also be understood that other forms of reflectors may also be employed such as individual segments of similar shapes, each symmetrical to the axis. Spherical reflectors can also be utilized, and the oscillators of the sound generating unit can be triggered separately in each plane perpendicular to the axis so that a therapy field focused in a true-phased manner is yielded.

In addition, a reflector perpendicular to the axis running through the focal point may have an elliptical cross-section, and the cylindrical sound source may be arranged co-axially in the focal line of the reflector yielding in this manner a line-shaped focus which can be advantageous in various applications. With a reflector of axially symmetrical geometry, a line-shaped focus can also be generated by the cylindrical axis being at an angle relative to the axis of the reflector.

Furthermore, the surface of the reflector can be constructed such that generated surface waves do not interfere with the reflected waves. In this connection, reference is again made to DE-PS 32 41 026.

The size and the shape of the focal zone may not only be influenced by the selection of special materials and by the thickness of the material and shape of the reflector, but also by a correction area in the path of and through which the generated sound wave field is modified, thereby yielding a specific focal zone.

Within the fundamental concept of the present invention employing a surface sound generating unit to generate a wave field that is symmetrical to an axis running through the focal point and is essentially directed vertically away from this axis, various principles of sound generation may, of course, be used as long as they can only generate wave fields that are radially emitted on the casing surface of the sound generating unit.

By way of illustration, piezo-oscillators can be provided on the emission area of the sound generating unit to generate the sound field, or a radially polarized piezo-ceramic hollow cylinder can be used.

It is especially advantageous, however, to utilize an electromagnetic pressure wave generating unit, which generate a therapeutical sound field with high efficiency and great longevity.

In particular, a coil for raising the energy may be composed of several individual coils arranged within one another and connected electrically in parallel. An insulating layer is preferably arranged between the coil and the membrane, which to contribute in improving electrical safety.

The membrane can be made of a highly electrically conductive material, such as, for example, gold, silver, copper or alloys thereof. Very firm supporting material is electrically isolated from the membrane. Possible materials to select from for the supporting material are stainless steel, titanium or beryllium.

The support material can be firmly connected to the membrane to improve the sound emission properties.

It is within the scope of the present invention to make the thickness of the membrane and/or the support material not constant to permit setting the generated sound field within certain limits as desired.

Where a sound generating unit is provided with a piezo-oscillator for generating sound pulses further improvement can be obtained to overcome the general problem of generating a high-energy therapy wave with little energy density in the region of the emission area with the greatest possible efficiency.

In this connection, it is of special significance that at least one acoustically adapting layer is provided, which preferably can be a $\lambda/4$ layer and, in particular, can be composed of a fluid.

It is advantageous with regard to the present invention, if the piezo-oscillator is made of a multiplicity of piezo-elements, which are isolated from one another by oil. The electric triggering of the piezo-elements is, particularly with regard to the cylindrical geometry, simplified by a metal gauze or a foil, to establish electric contact with the piezo-elements.

In this event, the contact material can be pressed against the piezo-elements, in particular, by low-pressure or by a bias and can simultaneously serve as an adapting layer and especially as a $\lambda/4$ layer.

The improvement of an acoustically adapting layer is particularly simplified by differences in the height of the piezo-elements being compensated for by a thin, elastic or ductile material so that a particularly balanced configuration is obtained.

The according to the present invention may, of course, be utilized for lithotripters working with a patient's tub as is described in the literature. As, however, the apparatus of the present invention is very small and compact, it also can be utilized in an especially advantageous manner in tub-free lithotripters. In the latter case, it is particularly advantageous if the reflector is sealed off by a sound-permeable and acoustically adapting membrane and the coupling medium is, in a known manner, a medium with tissue-like acoustic properties and, in particular, a fluid.

BRIEF DESCRIPTION OF THE DRAWINGS

The objects, features and advantages of the present invention will be more apparent form the following detailed description of several preferred embodiments presently when taken in conjunction with to the accompanying drawings wherein, in which FIG. 1 is a schematic view of an apparatus for generating focused sound wave fields in accordance with the present invention;

FIGS. 2 to 4 show various ways of integrating the locating units in the apparatus shown in FIG. 1, and FIGS. 5*a* and *b* show two alternative embodiments of the sound generating unit in accordance with the apparatus of the present invention.

DETAILED DESCRIPTION OF THE DRAWINGS

Figure 2:
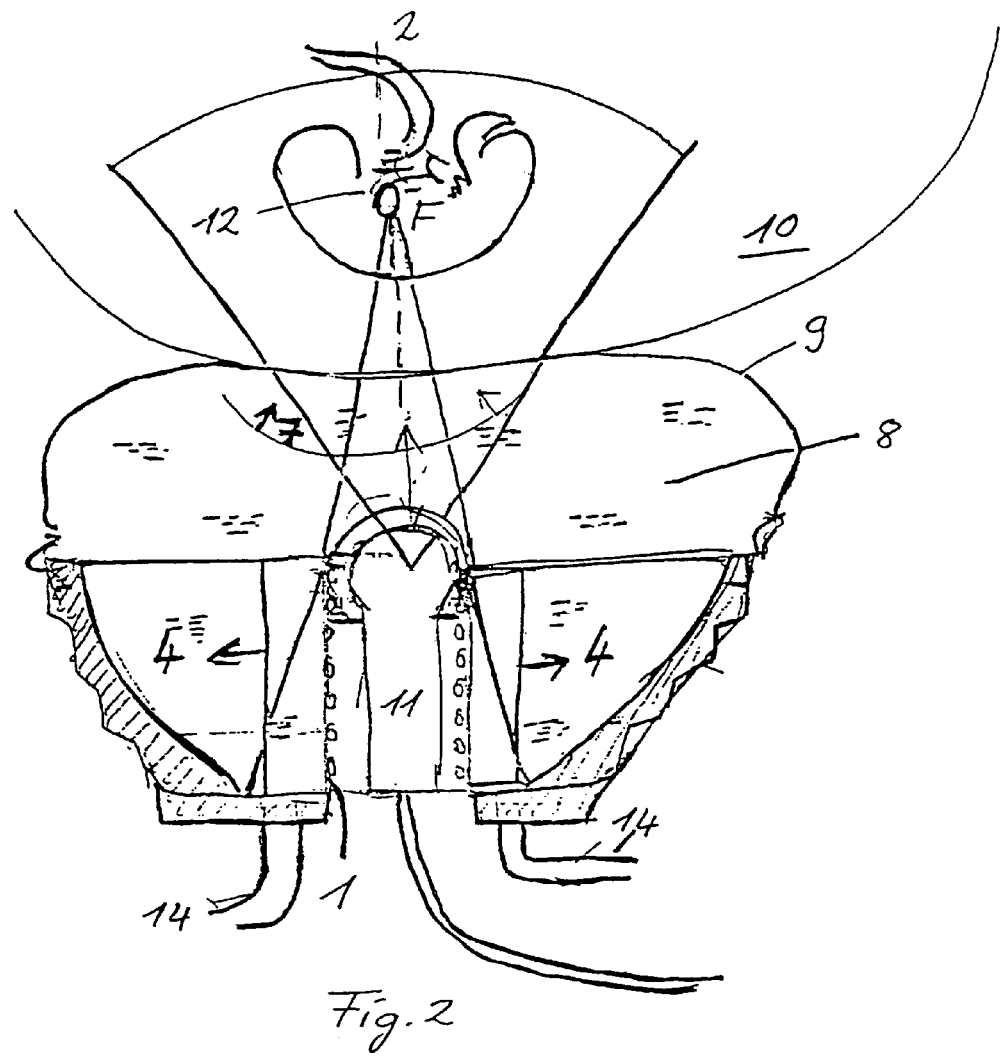

The apparatus for generating focused sound wave fields shown in FIG. 1, includes a sound generating unit 1 for a therapy wave field. The emission area 1' of the sound generating unit has cylindrical shape in the illustrated embodiment. An axially symmetrical reflector 3 is arranged coaxially with an axis 2 of the apparatus, which also coincides with the axis of the cylindrical emission surface 1', and has the inner surface the shape of a parabola.

The sound generating unit generates cylindrical wave fronts 4 moving away in the radial direction 5 from the sound generating unit 1. Following reflection of the wave fronts at the reflector 3 having the paraboloid inner contour, focused wave fields 7 are produced with an aperture angle of α, and which converge at the focal point F, thereby generating therapeutically effective power densities at the focal point F.

The shape 6 in every section of the reflector 3 containing the axis 2 is given by the following equation:

$$Y^2 = 2px$$

whereby p is the distance of the focal point F from the origin of the coordinates; the position of the coordinate system used as seen in FIG. 1.

If the acoustical therapy waves have very high amplitudes, their propagation behavior may deviate from linear propagation behavior so that changes in the focal geometry can result. These changes in focal geometry can be compensated for by corresponding adaption of the reflector area, for example, by minimal deviations from the parabola shape. In the same manner, precise changes in the focused therapy wave field can be attained by defined deviations from the parabola shape and/or by corresponding changes in the reflection behavior of the surface. Additionally, a correction area 3", shown in phantom has a predetermined phase structure and is provided to extend or shift the focusing zone in a predetermined manner. The modification of the reflector is accomplished prior to therapeutic application.

Depending on whether a reflection of the wave with or without phase inversion is aimed at, a material is selected for the reflector, which is acoustically harder, respectively softer, than the coupling fluid. In the event, predominantly positive pressure pulses are generated, e.g. for extra-corporeal lithotripsy, it is advantageous to provide a source, which generates positive pressure pulses, with an acoustically hard reflector. Depending on the therapeutical goal, other source/reflector combinations may be useful. For the extra-corporeal lithotripsy, a brass reflector in combination with water as the coupling fluid has much to recommend it.

In the selection of the reflector material, moreover, attention must be paid in addition to the already mentioned characteristics that the propagation speed for transverse surface waves is smaller or minimally larger than the propagation speed of the therapy waves in the coupling fluid.

FIG. 2 depicts, by way of example, the apparatus for generating focused sound wave fields shown in FIG. 1 supplemented with additional function elements for utilization as a lithotripter. In particular, within the cylindrical emission area 1' of the sound generating unit there is an ultrasonic locating device 11, e.g. in the form of an ultrasonic-B-image device, which serves to represent the focal zone F in the body of a living being 10.

In FIG. 2 the sound generating unit is shown, by way of example without the intention of limiting the overall inventive concept, as an electromagnetic system provided with a coil 1" within the emission area 1. Of course, other elements may also be used for sound generation, such as piezo-electric sources with a cylindrical shape.

For coupling sound waves in bodies of living beings, it is advantageous to generate the waves already in a medium with tissue-like acoustic properties in order to keep reflection losses low. Media of this kind are, for example, water, oils or other fluids, the acoustic impedances δ*c (density*sonic speed) of which approach the impedance of living tissue in the coupling region of the therapy wave. For this reason, reflector 3 in FIG. 2 is sealed by a sound-permeable, acoustically adapted membrane 9. A coupling fluid is provided the space 8 formed by the reflector 3 and the membrane 9 so that a flexible cushion is yielded, which is acoustically coupled to a body 10 while avoiding gas occlusions.

Therapy waves 4 propagate first radially in reference to the axis of rotation 2 of the system and are subsequently reflected by reflector 3 to the focal point F. The acoustic reflector 3 has the parabolic shape and is composed of a material with a high degree of reflection in comparison with the coupling fluid 8.

The acoustically focused wave field 7 is coupled into the body 10 via the membrane 9 and aligned to the therapeutic target area 12 with the aid of the ultrasonic locating unit 11. For optimizing the image quality of the ultrasonic image, the ultrasonic probe is arranged along the axis 2 in such a manner that it is moveable in the direction of the double-headed arrow so that it can selectively be moved toward the body or drawn away therefrom in order to avoid shading the therapy wave field. A corresponding position sensor assures that the focal point of the therapy field is continuously represented in the ultrasonic image. Moreover, the ultrasonic probe is arranged rotatably about axis 2 so that the ultrasonic image can selectively represents various section planes. The therapy unit has, in addition to the necessary supply connections for the therapy source, ultrasonic probe connections 14 for balancing the volume of the coupling cushion by adding or removing suitably prepared coupling fluids so that acoustically favorable application of membrane 9 to the body 10 is possible. Supply devices such as conventional pumps, control units, degassing instruments, etc., are not shown for clarity purposes and conciseness.

FIG. 3 shows another embodiment of the present invention in which the ultrasound probe is replaced by an X-ray locating device. The same numerals are used to describe parts similar to those used in FIGS. 1 and 2. The X-ray tube 15 is connected to the therapy unit such that the focus of the X-ray tube 15 is on the axis of rotation 2. For the alignment of the therapy field on the target area 12, a target marking 16 is arranged on the axis 2, which is imaged together with the target area 12 in the X-ray recording plane 18, in which, by way of example, an image amplifier or an X-ray film is arranged. As a result, adjustment of the target area on the axis 2 is possible. Adjusting the target area in the axial direction to the focal point F can occur by an additional X-ray projection in an inclined direction. The pitch if the X-ray axis is selected in such a way that, on the one hand, the target area remains in the X-ray picture field without being completely shaded by the geometry of the therapy source 1 and, on the other hand, focal point F is selected as the center of rotation.

The target marking 16 is pivoted in the same manner with the center beam of the X-ray projection. The target area is subsequently brought to coincide with the therapy focus if under two inclined X-ray projection directions in each case the target area is imaged in the same position with the target marking.

An advantageous embodiment is yielded if instead of the X-ray tub swinging about the therapy focus F, a tube with two spacially separate focii is employed in conjunction with two adapted target markings.

Other advantageous embodiments are obtained where both the X-ray pictures generated at different projection angles are represented and observed with the assistance of state of the art representation techniques in the form of stereo-scopic images for the special alignment of the therapy focus on the target area.

In order to improve X-ray quality, an additional device 17 can be provided, for example, of an inflatable balloon which displaces the coupling fluid out of the path of the X-ray projection beam while the X-ray image is being generated.

Figure 4:
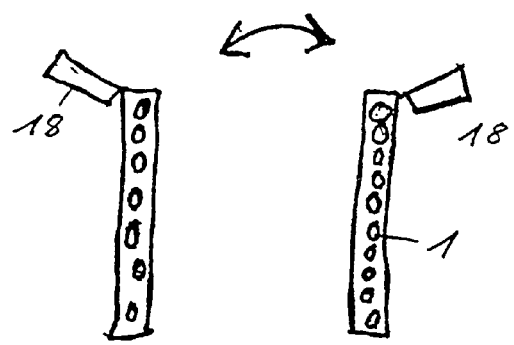

FIG. 4 shows a therapy system of the present invention having an X-ray and an ultrasonic locating device such that an annular ultrasonic probe 18 of generally known construction such as a B-image generation, which is adapted to the geometry of therapy source 1 is attached. By sweeping about a horizontal axis of rotation, a B-image of the highest lateral resolution can be generated in the manner of a sector scanner known from medical ultrasonic technology. Finally, instead of a mechanically pivoting of the annular ultrasonic transducer 18, a linearly sub-divided electronically triggered circular array (annular array) having a large opening in the center can be utilized or a radially segment array with which a three-dimensional scanning and locating unit can be realized by electronically deflecting the ultrasonic locating field.

Figure 5B:
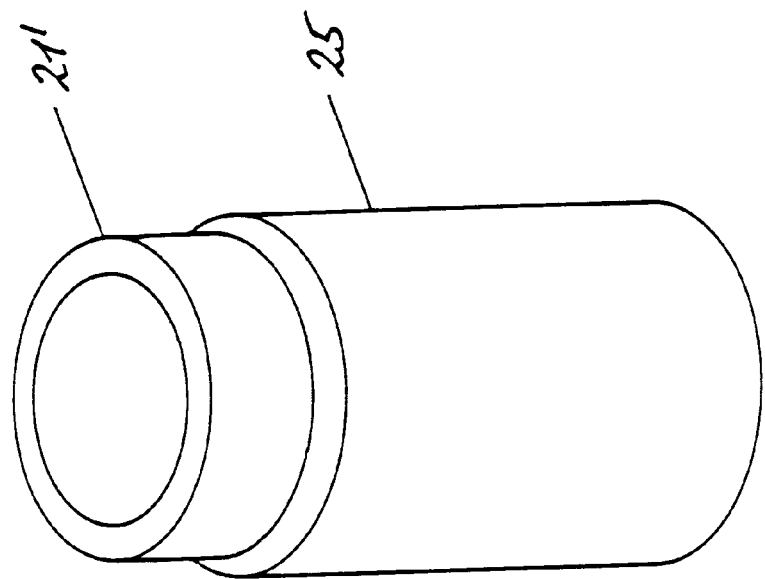
Figure 5A:
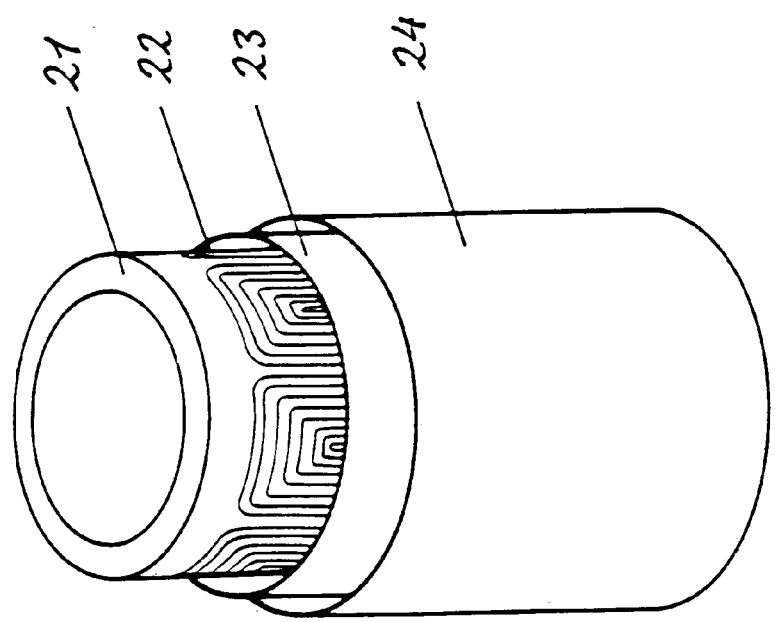

FIGS. 5a and 5b show two exemplary embodiments of the sound generating unit 1 used in the present invention. An electromagnetic pulse sound generating unit provided with a barrier 21 for a coil 22 is depicted in FIG. 5a. Coil 22 is comprises of several individual coils arranged within one another and electrically connected in parallel for raising the energy. Furthermore, a membrane 24, and in particular a metal membrane, is provided as the actual "sound emission area". An insulating layer 23 is arranged between coil 22 and membrane 24 and especially contributes to improvement in electrical safety. The membrane usually is made of a highly electrically conductive material, as by way of illustration gold, silver or alloys thereof. The very firm supporting material 21, which is electrically insulated from the membrane, may, for example, be stainless steel, titanium or beryllium.

FIG. 5b depicts an embodiment, in which a radially polarized piezo-ceramic cylinder 25 is arranged on a barrier 21'. In addition, an adapting layer not shown is provided.

Figure 7:
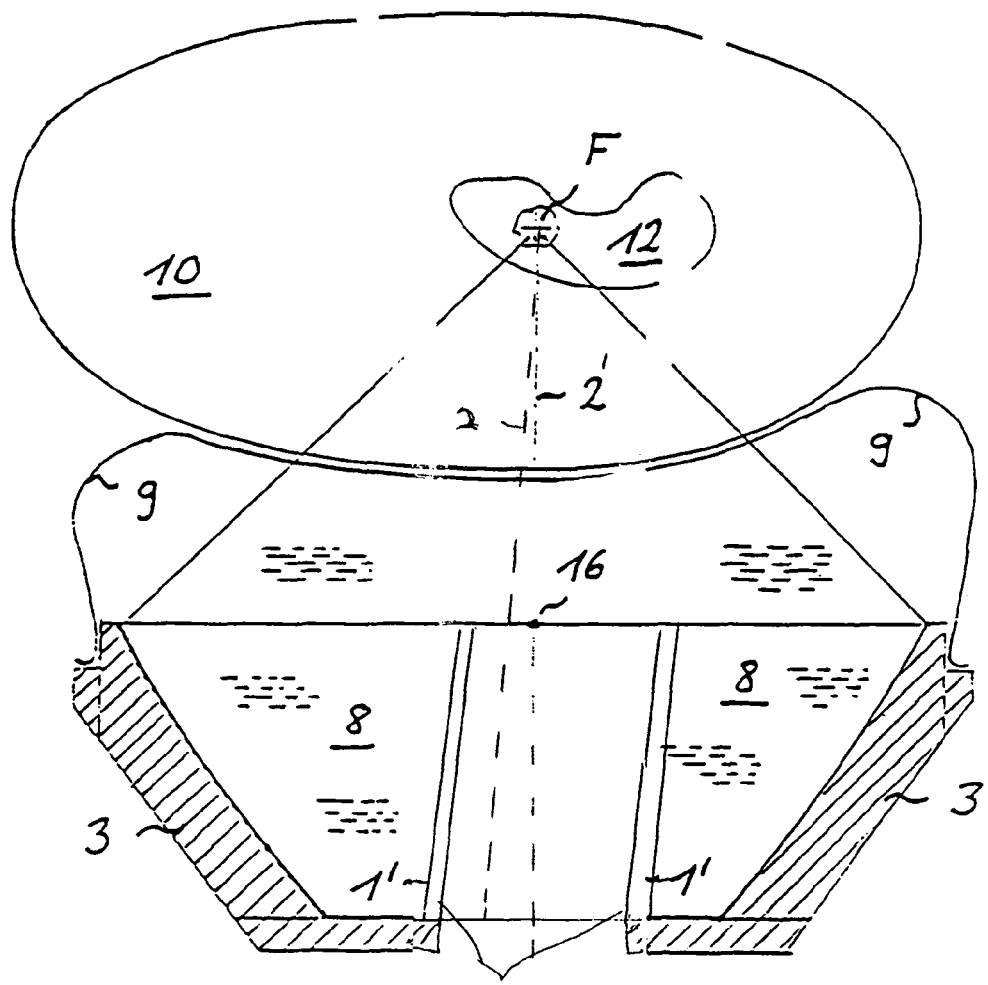
FIG. 7 shows a further alternative embodiment of the sound generating unit.

With the above-described apparatuses with, for example, an aperture angle of 83° and a focal distance of 15 cm, a focal zone of 6 mm lateral and 30 mm axial, i.e. dimensions well-adapted to the fragmentation requirements, can be obtained, whereby the pressure amplitudes reach 90 MPa at pressure increase periods of approx. 100 ns. As an alternative to the coaxial cylindrical sound source and reflector axis of the previous figures, FIG. 7 shows a modified embodiment. With reflector 3 of axial symmetrical geometry, a line-shaped focus can also be generated by the cylindrical axis 2 of the cylindrical sound source 1 being at an angle relative to the axis 2' of the reflector 3. Both axis run through the focal point F.

Figure 6:
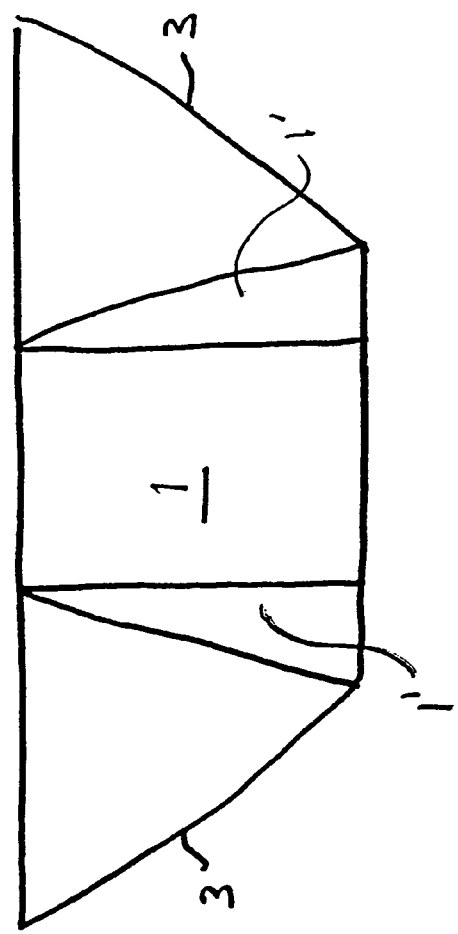
FIG. 6 shows an alternative embodiment of the sound generating unit.

FIG. 6 shows a truncated cone which may be used as sound generating unit 1 in the embodiments of the previous figures.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. An apparatus for generating focused, acoustical pressure waves for therapeutical application comprising:
    a coupling medium;
    a reflector having an axis which focuses the waves at a single focal point on said axis;
    a sound generator operative to generate pressure waves in said coupling medium and located within an interior of said reflector;
    wherein said sound generator is a body axially symmetrical to an axis running through the focal point and includes a casing extending in the direction of said axis and constituting the emission area for said waves; and
    wherein said sound generator generates axially symmetrical waves symmetrical to said axis and whose propagation direction is essentially perpendicular to said axis.

2. An apparatus according to claim 1, wherein said body is hollow.

3. An apparatus according to claim 2, wherein said hollow body has one of a cylindrical shape and a truncated cone shape.

4. An apparatus according to claim 1, wherein said reflector has a paraboloid shape, whose axis of revolution intersects said sound generator in the region of said axis.

5. An apparatus according to claim 1, wherein said sound generator is an electromagnetic pressure wave generating unit.

6. An apparatus according to claim 1, wherein said sound generator is a piezoelectric pressure wave generating unit.

7. An apparatus according to claim 6, wherein said piezoelectric pressure wave generating unit includes piezoelectric oscillators located at said emission area.

8. An apparatus according to claim 7, wherein said oscillators are triggered separately in planes perpendicular to said axis.

9. An apparatus according to claim 1, wherein at least one locating unit is arranged within said axially symmetrical emission area of said sound generator.

10. An apparatus according to claim 1, wherein said sound generator is a piezo-oscillator which is stimulated by a pulse generator and further includes an oscillatable membrane which emits ultrasonic pulses, and
    at least one acoustically adapting layer operatively associated therewith.

11. An apparatus according to claim 10, wherein said at least one adapting layer is a $\lambda/4$ layer.

12. An apparatus according to claim 11, wherein said at least one adapting layer is composed of a fluid.

13. An apparatus according to claim 10, wherein said piezo-oscillator comprises a plurality of piezo-elements isolated from each other by oil.

14. An apparatus according to claim 13, wherein said piezo-elements are electrically contacted by one of a metal gauze material or a foil material.

15. An apparatus according to claim 14, wherein said electrical contact material is pressed against said piezo-elements.

16. An apparatus according to claim 14, wherein said electrical contact material is a $\lambda/4$ layer.

17. An apparatus according to claim 13, wherein the plurality of piezo-elements have a height difference compensated for by a thin elastic or ductile material.

18. An apparatus for generating focused, acoustical pressure waves for therapeutical application comprising:
    a coupling medium;
    a sound generator operative to generate pressure waves in said coupling medium;
    a reflector having an axis which focuses the waves at a focal point on said axis; and
    at least one locating unit for locating concrements, corporeal stones and objects to be destroyed;
    wherein said sound generator is a body axially symmetrical to an axis running through the focal point and includes a casing extending in the direction of said axis and constituting the emission area for said waves;

wherein said sound generator generates axially symmetrical waves symmetrical to said axis and whose propagation direction is essentially perpendicular to said axis;

wherein said at least one locating unit is arranged within said axially symmetrical emission area of said sound generator; and wherein said at least one locating unit is an X-ray unit.

19. An apparatus for generating focused, acoustical pressure waves for therapeutical application comprising:
a coupling medium;
a sound generator operative to generate pressure waves in said coupling medium;
a reflector having an axis which focuses the waves at a single focal point on said axis; and
at least one locating unit for locating concrements, corporeal stones and objects to be destroyed;
wherein said sound generator is a body axially symmetrical to a axis running through the focal point and includes a casing extending in the direction of said axis and constituting the emission area for said waves; and
wherein said sound generator generates axially symmetrical waves symmetrical to said axis and whose propagation direction is essentially perpendicular to said axis;
wherein said at least one locating unit is arranged within said axially symmetrical emission area of said sound generator.

20. An apparatus according to claim 10, wherein said at least one locating unit is an ultrasonic, B-image generating locating unit.

21. An apparatus according to claim 19, including means for moving said at least one locating unit along or rotated about said axis.

22. An apparatus for generating focused, acoustical pressure waves for therapeutical application comprising:
a coupling medium;
a sound generator operative to generate pressure waves in said coupling medium;
a reflector having an axis which focuses the waves at a single focal point on said axis;
wherein said sound generator is a body axially symmetrical to said axis running through the focal point and includes a casing extending in the direction of said axis and constituting the emission area for said waves;
wherein said sound generator generates axially symmetrical waves symmetrical to said axis and whose propagation direction is essentially perpendicular to said axis; and
wherein said reflector is configured such that the generated waves do not interfere with waves reflected by said reflector.

23. An apparatus for generating focused, acoustical pressure waves for therapeutical application comprising:
a coupling medium;
a sound generator operative to generate pressure waves in said coupling medium;
a reflector having an axis which focuses the waves at a single focal point on said axis;
wherein said sound generator is a body axially symmetrical to said axis running through the focal point and includes a casing extending in the direction of said axis and constituting the emission area for said waves;
wherein said sound generator generates axially symmetrical waves symmetrical to said axis and whose propagation direction is essentially perpendicular to said axis; and
wherein said reflector is sealed by a sound-permeable and acoustically adapted membrane.

24. An apparatus for generating focused, acoustical pressure waves for therapeutical application comprising:
a coupling medium;
a sound generator operative to generate pressure waves in said coupling medium;
a reflector having an axis which focuses the waves at a single focal point on said axis;
wherein said sound generator is a body axially symmetrical to said axis running through the focal point and includes a casing extending in the direction of said axis and constituting the emission area for said waves;
wherein said sound generator generates axially symmetrical waves symmetrical to said axis and whose propagation direction is essentially perpendicular to said axis; and
wherein said coupling medium has tissue-like acoustic properties.

25. An apparatus according to claim 24, wherein said coupling medium is a fluid.

26. An apparatus for generating focused, acoustical pressure waves for therapeutical application comprising:
a coupling medium;
a sound generator operative to generate pressure waves in said coupling medium;
a reflector having an axis which focuses the waves at a focal point on said axis;
wherein said sound generator is a body axially symmetrical to said axis running through the focal point and includes a casing extending in the direction of said axis and constituting the emission area for said waves;
wherein said sound generator generates axially symmetrical waves symmetrical to said axis and whose propagation direction is essentially perpendicular to said axis; and
a correction area, on said casing, having a predeterminable phase structure is provided to extend or shift the focal point in a defined manner.

27. An apparatus for generating focused, acoustical pressure waves for therapeutical application comprising:
a coupling medium;
a sound generator operative to generate pressure waves in said coupling medium;
a reflector having first axis which focuses the waves at a single focal point on said first axis;
wherein said sound generator is a hollow body axially symmetrical to a second axis running through the focal point and includes a casing extending in the direction of said second axis and constituting the emission area for said waves;
wherein said sound generator generates axially symmetrical waves symmetrical to said second axis and whose propagation direction is essentially perpendicular to said second axis; and
wherein the hollow body's second axis is at an angle relative to the first axis of the reflector.

28. An apparatus for generating focused, acoustical pressure waves for therapeutical application comprising:
a coupling medium;
a sound generator operative to generate pressure waves in said coupling medium;
a reflector having an axis which focuses the waves at a single focal point on said axis;
wherein said reflector has a circular cross-section perpendicular to said axis running through said focal point;
wherein said sound generator is a cylinder co-axial with said axis of said reflector and includes a casing extending in the direction of said axis and constituting the emission area for said waves; and wherein said sound generator generates axially symmetrical waves symmetrical to said axis and whose propagation direction is essentially perpendicular to said axis.

29. An apparatus for generating focused, acoustical pressure waves for therapeutical application comprising:
a coupling medium;
a sound generator operative to generate pressure waves in said coupling medium;
a reflector having an axis which focuses the waves at a single focal point on said axis;
wherein said sound generator is a body axially symmetrical to said axis running through the focal point and includes a casing extending in the direction of said and constituting the emission area for said waves;
wherein said sound generator generates axially symmetrical waves symmetrical to said axis and whose propagation direction is essentially perpendicular to said axis; and
wherein said sound generator is an electromagnetic generator having a coil adapted to be stimulated by a pulse generator, and an oscillatable membrane which emits ultrasonic pulses.

30. An apparatus according to claim 29, wherein an insulating layer is arranged between said coil and said membrane.

31. An apparatus according to claim 29, wherein said membrane comprises an electrically conductive supporting material supported by a firm material.

32. An apparatus according to claim 31, further including electrical isolation for electrically isolating said firm supporting material from said membrane.

33. An apparatus according to claim 31, wherein said supporting material is a metal or plastic material.

34. An apparatus according to claim 31, wherein said supporting material is magnetizable.

35. An apparatus according to claim 31, wherein said supporting material is attached to the membrane.

36. An apparatus according to claim 31, wherein the thickness of at least one of said membrane and said supporting material varies.

37. An apparatus according to claim 31, wherein at least one of said membrane and said supporting material is pressed against said coil.

38. An apparatus according to claim 31, wherein at least one of said membrane and said supporting material is embedded in elastic material.

39. An apparatus according to claim 29, wherein said membrane is provided with at least one corrugation.

40. An apparatus according to claim 29, wherein said coil comprises several individual coils electrically connected in parallel.

41. An apparatus for generating focused, acoustical pressure waves for therapeutical application comprising:
a coupling medium;
a reflector having an axis which focuses the waves at a single focal point on said axis;
a sound generator operative to generate pressure waves in said coupling medium and located within an interior of said reflector;
wherein said sound generator is a body axially symmetrical to an axis running through the focal point and includes a casing extending in the direction of said axis and constituting the emission area for said waves;
wherein said sound generator generates axially symmetrical waves symmetrical to said axis and whose propagation direction is essentially perpendicular to said axis; and
wherein said sound generator is an electromagnetic pressure wave generating unit; and
wherein said reflector has a paraboloid shape, whose axis of revolution intersects said sound generator in the region of said axis.

42. An apparatus for generating focused, acoustical pressure waves for therapeutical application comprising:
a coupling medium;
a reflector having an axis which focuses the waves at a single focal point on said axis;
a sound generator operative to generate pressure waves in said coupling medium and located within an interior of said reflector;
a membrane coupled to the reflector;
wherein the coupling medium is contained between the reflector and the membrane;
wherein said sound generator is a body axially symmetrical to an axis running through the focal point and includes a casing extending in the direction of said axis and constituting the emission area for said waves;
wherein said sound generator generates axially symmetrical waves symmetrical to said axis and whose propagation direction is essentially perpendicular to said axis; and
wherein said sound generator is an electromagnetic pressure wave generating unit; and
wherein said reflector has a paraboloid shape, whose axis of revolution intersects said sound generator in the region of said axis.

* * * * *